United States Patent
Lam et al.

(10) Patent No.: US 9,693,754 B2
(45) Date of Patent: *Jul. 4, 2017

(54) IMAGING PROCESSING SYSTEMS AND METHODS

(71) Applicant: ACIST Medical Systems, Inc., Eden Prairie, MN (US)

(72) Inventors: Duc H. Lam, San Jose, CA (US); Thomas C. Moore, Livermore, CA (US); Kendall R. Waters, Livermore, CA (US)

(73) Assignee: ACIST Medical Systems, Inc., Eden Prairie, MN (US)

( * ) Notice: Subject to any disclaimer, the term of this patent is extended or adjusted under 35 U.S.C. 154(b) by 210 days.

This patent is subject to a terminal disclaimer.

(21) Appl. No.: 13/894,927

(22) Filed: May 15, 2013

(65) Prior Publication Data

US 2014/0343430 A1 Nov. 20, 2014

(51) Int. Cl.
*A61B 8/00* (2006.01)
*A61B 8/08* (2006.01)
*A61B 8/12* (2006.01)

(52) U.S. Cl.
CPC .......... *A61B 8/5207* (2013.01); *A61B 8/0891* (2013.01); *A61B 8/12* (2013.01); *A61B 8/445* (2013.01); *A61B 8/4461* (2013.01); *A61B 8/5246* (2013.01); *A61B 8/5269* (2013.01)

(58) Field of Classification Search
None
See application file for complete search history.

(56) References Cited

U.S. PATENT DOCUMENTS

| 4,347,443 | A | | 8/1982 | Whitney |
| 4,850,363 | A | | 7/1989 | Yanagawa |
| 4,860,758 | A | | 8/1989 | Yanagawa et al. |
| 4,949,310 | A | * | 8/1990 | Smith et al. ............ 367/7 |
| 5,070,735 | A | | 12/1991 | Reichert et al. |

(Continued)

FOREIGN PATENT DOCUMENTS

| CN | 101208045 A | 6/2008 |
| EP | 346889 A1 | 1/1995 |

(Continued)

OTHER PUBLICATIONS

Vishruta et al. "Use of frequency diversity and Nakagami statistics in ultrasound tissue characterization", IEEE, vol. 48, No. 5, Sep. 2001.*

(Continued)

*Primary Examiner* — Katherine Fernandez
*Assistant Examiner* — Marjan Saboktakin
(74) *Attorney, Agent, or Firm* — Fredrikson & Byron, P.A.

(57) ABSTRACT

Systems and methods for image processing based on ultrasound data. The system may include an IVUS catheter configured to collect data vectors including ultrasound data and an imaging engine configured to process the ultrasound data of the data vectors. The imaging engine may receive the data vectors and divide the data vectors into different sets. The ultrasound data of each respective set may be averaged and then an envelope of each set may be detected. The envelopes of each set may then be averaged to generate an enhanced data vector which may be used to generate an image.

28 Claims, 11 Drawing Sheets

(56) References Cited

U.S. PATENT DOCUMENTS

| | | | |
|---|---|---|---|
| 5,131,396 A * | 7/1992 | Ishiguro et al. | 600/459 |
| 5,203,338 A | 4/1993 | Jang | |
| 5,363,849 A * | 11/1994 | Suorsa et al. | 600/454 |
| 5,396,285 A | 3/1995 | Hedberg et al. | |
| 5,531,679 A | 7/1996 | Schulman et al. | |
| 5,741,552 A | 4/1998 | Takayama et al. | |
| 5,833,615 A | 11/1998 | Wu et al. | |
| 5,848,969 A | 12/1998 | Panescu et al. | |
| 5,876,343 A | 3/1999 | Teo et al. | |
| 6,132,374 A | 10/2000 | Hossack et al. | |
| 6,139,501 A | 10/2000 | Roundhill et al. | |
| 6,216,025 B1 * | 4/2001 | Kruger | 600/407 |
| 6,645,147 B1 | 11/2003 | Jackson et al. | |
| 7,194,294 B2 * | 3/2007 | Panescu et al. | 600/374 |
| 7,691,061 B2 * | 4/2010 | Hirota | 600/443 |
| 2001/0029336 A1 | 10/2001 | Teo | |
| 2003/0063787 A1 | 4/2003 | Natanzon et al. | |
| 2003/0078497 A1 | 4/2003 | Ji et al. | |
| 2003/0208123 A1 | 11/2003 | Panescu | |
| 2004/0030250 A1 | 2/2004 | Stewart | |
| 2004/0037164 A1 | 2/2004 | Garlick et al. | |
| 2004/0199047 A1 | 10/2004 | Taimisto et al. | |
| 2005/0215897 A1 | 9/2005 | Sakaguchi et al. | |
| 2006/0253028 A1 | 11/2006 | Lam et al. | |
| 2007/0016068 A1 | 1/2007 | Grunwald et al. | |
| 2008/0015569 A1 | 1/2008 | Saadat et al. | |
| 2008/0200815 A1 | 8/2008 | Van Der Steen et al. | |
| 2009/0088830 A1 | 4/2009 | Mohamed et al. | |
| 2009/0284332 A1 | 11/2009 | Moore et al. | |
| 2010/0174190 A1 * | 7/2010 | Hancock et al. | 600/443 |
| 2010/0312109 A1 | 12/2010 | Satoh | |
| 2013/0109968 A1 | 5/2013 | Azuma | |

FOREIGN PATENT DOCUMENTS

| | | |
|---|---|---|
| EP | 1387317 A1 | 2/2004 |
| EP | 1609423 A2 | 12/2005 |
| EP | 2488107 A2 | 8/2012 |
| JP | H09000522 A | 1/1997 |
| JP | 2002530143 A | 9/2002 |
| JP | 2004180784 A | 7/2004 |
| JP | 2006014938 A | 1/2006 |
| JP | 2007229015 A | 9/2007 |
| JP | 2008508970 A | 3/2008 |
| JP | 2008536638 A | 9/2008 |
| JP | 2009545406 A | 12/2009 |
| JP | 4648652 B2 | 3/2011 |
| JP | 2013507227 A | 3/2013 |
| WO | 2006015877 A1 | 2/2006 |
| WO | 2006113857 A1 | 10/2006 |
| WO | 2006122001 A2 | 11/2006 |
| WO | 2008016992 A1 | 2/2008 |
| WO | 2011046903 A1 | 4/2011 |
| WO | 2014186268 A1 | 11/2014 |

OTHER PUBLICATIONS

S.W. Smith and O.T. von Ramm, "The Maltese Cross Processor: Speckle Reduction for Circular Transducers," Ultrasonic Imaging 10, 153-170, Jul. 2, 1988, 18 pages.

P. Mohana Shankar, et al., "Computer-Aided Classification of Breast Masses in Ultrasonic B-Scans Using a Multiparameter Approach," IEEE Transactions on Ultrasonics, Ferroelectrics, and Frequency Control, vol. 50, Aug. 2, 2003, 8 pages.

Hector M. Garcia-Garcia, et al., "Imaging of Coronary Atherosclerosis: Intravascular Ultrasound," European Heart Journal (2010) Sep. 7, 2010, 18 pages.

Kendall R. Waters, et al., "Development of a High-Definition Intravascular Ultrasound Imaging System and Catheter," 2011 IEEE International Ultrasonics Symposium Proceedings, Oct. 18, 2011, 4 pages.

Yao Wang, "Optimizing the Beam Pattern of a Forward-Viewing Ring-Annular Ultrasound Array for Intravascular Imaging," IEEE Transactions on Ultrasonics, Ferroelectrics, and Frequency Control., vol. 49, No. 12, Dec. 2, 2002, 14 pages.

International Search Report and Written Opinion for International Application No. PCT/US2014/037659, Aug. 28, 2014, 14 pages.

Foster, "Transducer Materials and Probe Construction," Ultrasound in Medicine and Biology, vol. 26, Supp. 1, 2000, pp. S2-S5.

Frijlink et al., "High Frequency Harmonic Imaging in Presence of Intravascular Stents," IEEE Ultrasonics Symposium, 2003, pp. 208-211.

Seo et al., "Sidelobe Suppression in Ultrasound Imaging Using Dual Apodization with Cross-Correlation," IEEE Transactions on Ultrasonics, Ferroelectrics, and Frequency Control, vol. 55, No. 10, Oct. 2008, pp. 2198-2210.

U.S. Appl. No. 61/218,177, titled Vector Domain Image Enhancement for Mechanically Rotating Imaging Catheters, filed Jun. 18, 2009.

Van Der Steen et al., "IVUS Harmonic Imaging," Ultrasound in Medicine and Biology, vol. 26, Supp. 2, 2000, p. A90.

* cited by examiner

IMAGING PROCESSING SYSTEMS AND METHODS

BACKGROUND

Intravascular ultrasound (IVUS) imaging is a technique that emits acoustic energy from a transducer at the tip of a small catheter, which is guided into the coronary arteries of the heart or other internal structures in the body. Acoustic energy that is reflected from vascular tissues are received by the transducer and sent to the system console, where a high-resolution, cross-sectional image is displayed in real time. The IVUS technique provides in-vivo visualization of the vascular structures and lumens, including the coronary artery lumen, coronary artery wall morphology, and devices, such as stents, at or near the surface of the coronary artery wall. IVUS imaging may be used to visualize diseased vessels, including coronary artery disease. An IVUS catheter will, in general, employ at least one high frequency (10 MHz-60 MHz) ultrasound transducer that creates pressure waves for visualization. At least one transducer is typically housed within a surrounding sheath or catheter member and mechanically rotated for 360 degree visualization. IVUS system data may be affected by a variety of factors including, for example, electrical noise, thermal noise, speckle, and/or relative motion between the vessel and the catheter. These factors may affect the quality of an image generated based on the affected ultrasound data. For instance, portions of the image may appear blurry or artifacts may appear in the image.

SUMMARY

In certain embodiments a system including an ultrasound transducer configured to generate a plurality of data vectors by emitting acoustic energy and receiving a backscatter of the energy, each data vector including ultrasound data, an imaging engine including at least one processor, the imaging engine configured to receive the plurality of data vectors from the ultrasound transducer, form a first set of data vectors and a second set of data vectors from the plurality of data vectors, generate a first combination of data and a second combination of data based on the first set of data vectors and the second set of data vectors respectively, generate a first envelope and a second envelope based on the first combination of data and the second combination of data, respectively, generate a combined envelope based on the first envelope and the second envelope, and generate an image based on the combined envelope.

In some examples, the system may further include a catheter assembly configured to deliver the ultrasound transducer to an imaging area, and a patient interface module including a catheter interface, wherein the patient interface module is electrically connected to the imaging engine and is coupled to the catheter and the ultrasound transducer via the catheter interface, and wherein the patient interface module is configured to rotate the ultrasound transducer relative to the catheter assembly. In some examples the data vectors of the first and second set of data vectors are radially sequential. In some examples the ultrasound transducer is configured to generate a data vector every $2\pi/4096$ radians as it is rotated relative to the catheter assembly. In some examples the first set of data vectors includes two data vectors and the second set of data vectors includes two data vectors. In some examples the first set of data vectors includes four data vectors and the second set of data vectors includes four data vectors. In some examples the first set of data vectors and the second set of data vectors each include at least one common data vector. In some examples the first and second combination of data are each generated by averaging the ultrasound data associated with each data vector of the first and second set of data vectors, respectively. In some examples the combined envelope is generated by averaging the first envelope and the second envelope. In some examples the acoustic energy emitted by the ultrasound transducer is between 40-60 MHz.

In certain embodiments a method comprising receiving a plurality of data vectors, each data vector comprising ultrasound data, forming a first and second set of data vectors from the plurality of data vectors, generating a first combination of data and a second combination of data based on the first set of data vectors and the second set of data vectors, respectively, generating a first envelope and a second envelope based on the first combination of data and the second combination of data, respectively, generating a combined envelope based on the first envelope and the second envelope, and generating an image based on the combined envelope.

In certain embodiments a non-transitory computer-readable storage article having a computer-executable instructions stored thereon to cause at least one programmable processor to receive a plurality of data vectors wherein each data vector comprises ultrasound data, form a first set of data vectors and a second set of data vectors from the plurality of data vectors, generate a first combination of data and a second combination of data based on the first set of data vectors and the second set of data vectors, respectively, generate a first envelope and a second envelope based on the first combination of data and the second combination of data, respectively, generate a combined envelope based on the first envelope and the second envelope, and generate an image based on the combined envelope.

The details of one or more examples are set forth in the accompanying drawings and the description below. Other features, objects, and advantages will be apparent from the description and drawings, and from the claims.

BRIEF DESCRIPTION OF DRAWINGS

The following drawings are illustrative of particular examples of the present invention and therefore do not limit the scope of the invention. The drawings are not to scale (unless so stated) and are intended for use in conjunction with the explanations in the following detailed description. Examples of the present invention will hereinafter be described in conjunction with the appended drawings, wherein like numerals denote like elements.

DETAILED DESCRIPTION

The following detailed description is exemplary in nature and is not intended to limit the scope, applicability, or configuration of the invention in any way. Rather, the following description provides some practical illustrations for implementing examples of the present invention. Examples of constructions, materials, dimensions, and manufacturing processes are provided for selected elements, and all other elements employ that which is known to those of ordinary skill in the field of the invention. Those skilled in the art will recognize that many of the noted examples have a variety of suitable alternatives.

Generally, intravascular ultrasound (IVUS) techniques employ a catheter to deliver an ultrasound transducer to an area of interest within the body of a patient. The area of interest may be, for example, coronary arteries of the heart or other internal structures of the body. The ultrasound transducer may be configured to generate ultrasound data by emitting and receiving acoustic energy (e.g., radio frequency, or RF, waves). The ultrasound data may be processed to generate images of the area. In certain examples, ultrasound data may be affected by a variety of factors including, for example, electrical noise, thermal noise, speckle, and/or relative motion between the vessel and the catheter. These factors may affect the quality of an image generated based on the affected ultrasound data (e.g., portions of the image may appear blurry, the presence of image artifacts in the image, etc.). This application generally relates to image processing techniques that may be used to improve the quality of an image. While this application cites many IVUS examples, one skilled in the art will appreciate that the image processing techniques are not limited only to IVUS. Methods described in this application may also be utilized in other wave-based imaging techniques, for example phase-sensitive optical coherence tomography.

Figure 1:
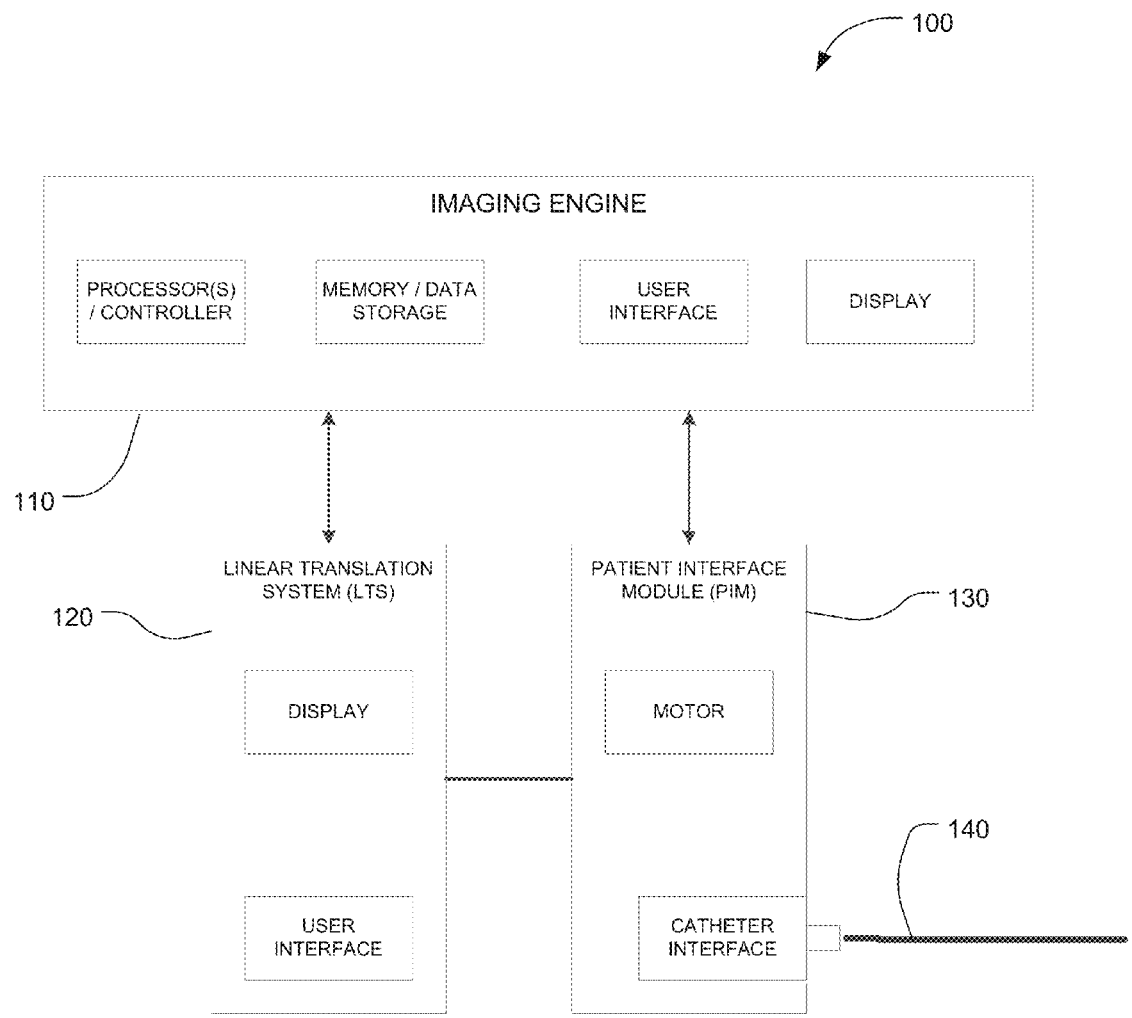
FIG. 1 is a block diagram of an example of an IVUS system.

FIG. 1 is a high-level block diagram of an example of an IVUS system 100. The IVUS system 100 includes an imaging engine 110, a patient interface module (PIM) 130, a linear translation system (LTS) 120, and an imaging catheter 140. The imaging engine 110 is the central component of the system and may perform one or more functions including, image generation, display of IVUS images and other information, control of the system components, storing and exporting the image data, a user interface (e.g., GUI) for operating the system, and analysis tools (e.g., area measurements, linear measurements, and annotations).

The PIM 130 provides the electromechanical interface between the catheter 140 and the imaging engine 110. The PIM 130 provides the mechanical interface to secure the catheter 140, as well as the mechanical energy to rotate an imaging assembly of the catheter 140. The PIM 130 also provides the electrical interface that transmits the signal from the integrated ultrasound generator to the catheter 140 and receives the return signal.

The catheter 140 is a minimally invasive intravascular ultrasound imaging catheter. The catheter 140 emits acoustic energy from a transducer at its distal tip, which is guided into the coronary arteries of the heart. Sound waves that are reflected from vascular tissues are received by the transducer and sent through the PIM 130 to the imaging engine 110. The catheter 140 can be operated at selected frequencies, such as 40 MHz or 60 MHz, depending on user preference. The catheter 140 includes a drive cable surrounded by a sheath. The proximal end of the catheter 140 connects to the PIM 130 and is mechanically rotated by the PIM 130. The distal end of the catheter 140 includes an imaging element connected to and rotated through 360 degrees by the drive cable. The imaging element may be a broadband ultrasound transducer that emits and receives acoustic energy (pressure waves) between 40 MHz and 60 MHz depending on the user-selectable settings. It can be appreciated that the frequency at which the ultrasound transducer emits and receives acoustic energy may vary based on the application. The drive cable contains an electrical transmission line that electrically connects the PIM 130 to the imaging element transducer. Since the drive cable is mechanically rotated by the PIM 130, the imaging element continuously scans (rotates) through 360 degrees.

To initiate image acquisition, the PIM 130 sends an electrical signal (e.g., high frequency pulse) through the transmission line to the imaging element transducer. During "live" imaging, this high frequency pulse is periodically and continuously sent to the transducer to excite the transducer. The transducer converts the electrical signal into an acoustic energy pulse or pressure wave. In some examples, the pressure wave is transmitted through an elongated imaging window of the catheter and into the adjacent vascular tissues. The vascular tissues interact with and reflect the pressure wave back through the imaging window and onto the transducer. The transducer converts the received acoustic energy (pressure wave) back into electrical energy. The electrical energy is then transmitted, via the transmission line embedded in the drive cable, back to the PIM 130 and then back to the imaging engine for signal processing and image reconstruction.

Some examples include a telescope assembly integrated into the catheter that allows the imaging of multiple regions of interest in a single procedure by advancing or retracting the imaging assembly without moving the catheter sheath. The transducer can also be longitudinally translated along the imaging window by extending and collapsing the telescope assembly. This system allows for imaging along a length of the artery without moving the catheter sheath. The longitudinal translation can be performed manually by the physician or under motorized control. Motorized longitudinal translation enables the acquisition of calibrated three-dimensional volume data. This allows the imaging engine 110 to accurately measure distances along the length of the artery under investigation.

In some examples, the longitudinal translation is provided by a Linear Translation System (LTS) 120 that mates with the PIM 130 and catheter 140 to enable pullback of the catheter imaging core at a controlled rate. The LTS 120 provides calibrated linear translation for measurements on the longitudinal image. The LTS 120 may feature a display, which indicates the linear distance traversed and the pullback speed, as well as controls for starting/stopping pullback, setting pullback speed, resetting linear distance traversed to zero, and switching to manual mode. In manual mode, the physician can freely move the catheter imaging core forward and backward. In another example, the LTS 120 may be configured to enable either pullback and/or push-forward of the catheter imaging core at a controlled rate. In yet another example, the LTS 120 may be configured to oscillate the catheter imaging core by alternately performing pullback and push-forward.

In some examples of the catheter 140, such as when the catheter is used for minimally invasive intravascular ultrasound imaging for the examination of human coronary pathology, the catheter 140 is a 6F guide catheter compatible device. The catheter 140 has a short monorail (<2.0 mm) guidewire engagement system compatible with commercially available 0.014 in guidewires. The monorail has a distal radiopaque marker that is located 8 mm from the distal end of the catheter. The catheter's distal tip entry profile is <2.0F. The catheter's crossing profile is 3.2F. The catheter's working length is 142 cm.

Figure 2:
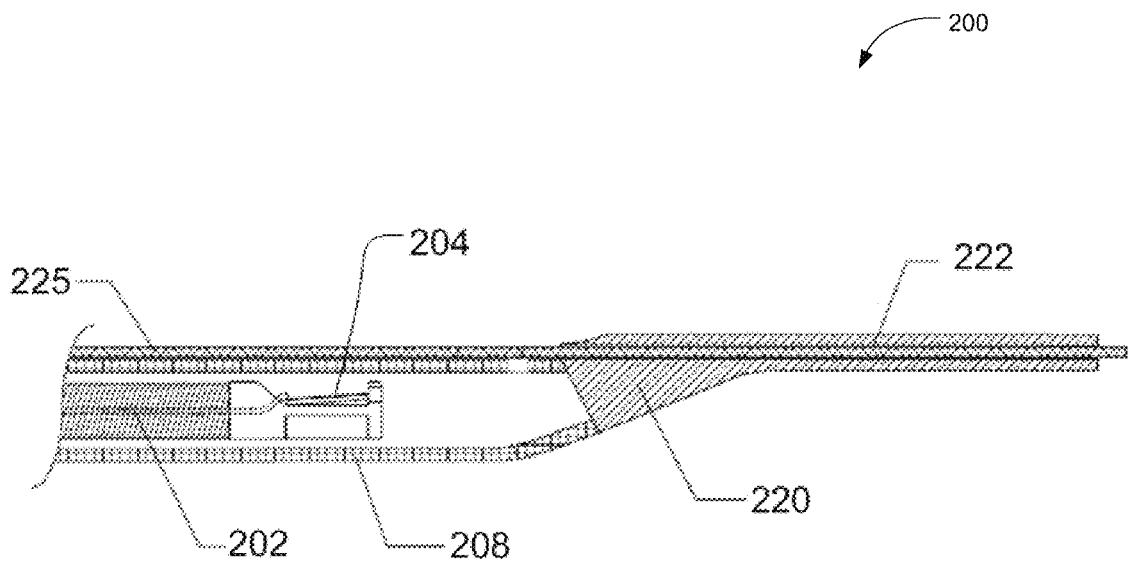
FIG. 2 is a side cross-sectional view of an IVUS catheter.

FIG. 2 is a side cross-sectional view of a distal end of a catheter 200 that may be used in system 100. Catheter 200 may include a drive cable 202, a sheath 208, and an ultrasound transducer 204. As noted above, the drive cable may be coupled to a PIM to rotate drive cable 202 within sheath 208. Ultrasound transducer 204 may be coupled to the drive cable such that the rotation of the drive cable also causes ultrasound transducer 204 to rotate within sheath 208. The ultrasound transducer may be configured to emit and receive acoustic energy during rotation to generate ultrasound data. In some examples, catheter 200 may also include an imaging window (not shown) substantially transparent to the frequency of the acoustic energy emitted by the ultrasound transducer. Catheter 200 may also include a distal end 220 forming a guidewire lumen 222 configured to accept a guidewire 225 to guide catheter 200 into a vascular system of a patient.

Figure 3:
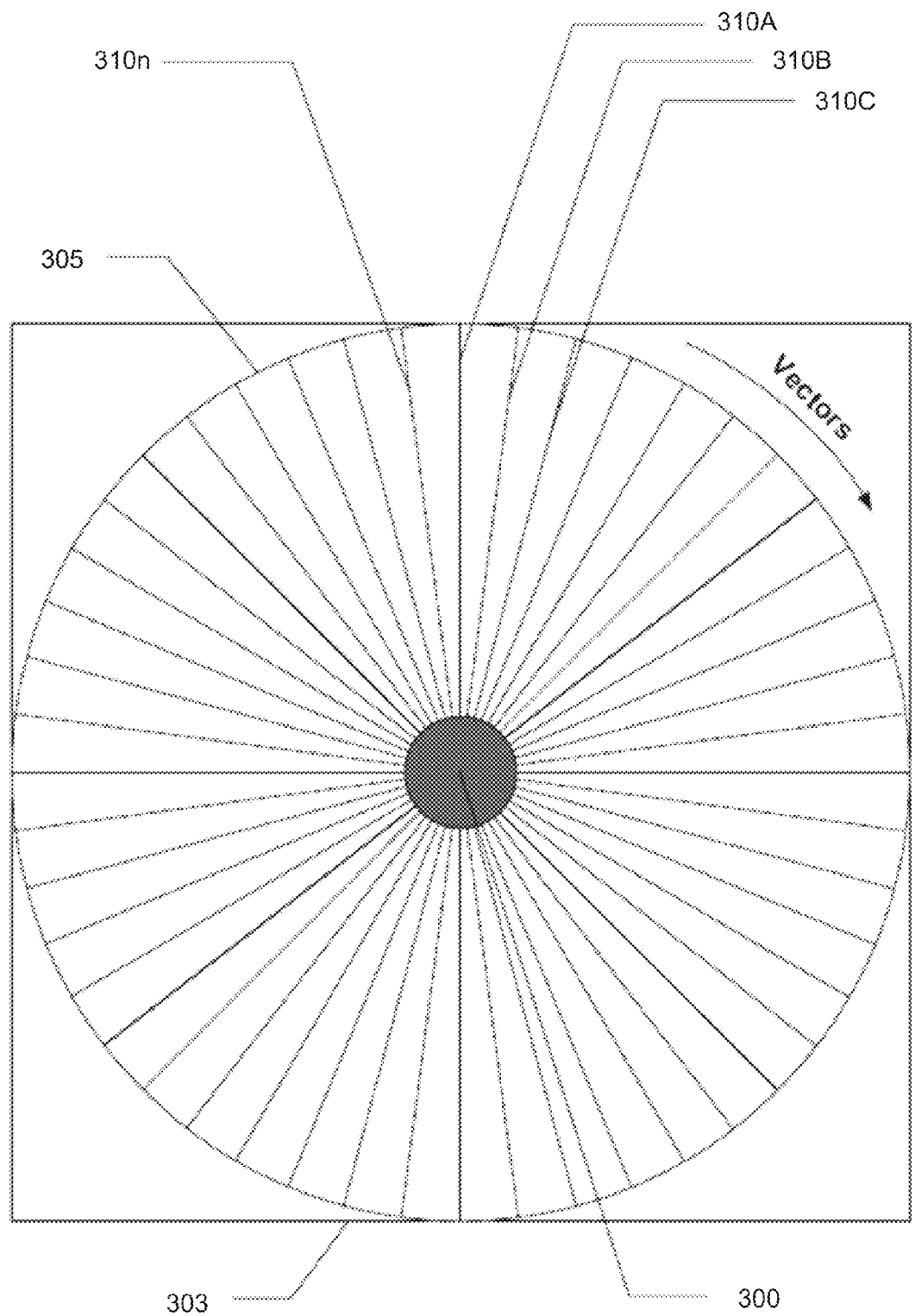
FIG. 3 is a front view of a catheter including data vectors propagated by the ultrasound transducer.

FIG. 3 is a front view of propagating ultrasound data vectors of a catheter 300. In this example, catheter 300 may be a mechanically rotating ultrasound imaging catheter similar to catheter 200 of FIG. 2. Similarly, catheter 300 may be configured to rotate an ultrasound transducer (not shown) relative to a sheath of catheter 300, and the ultrasound transducer may be configured to generate ultrasound data by emitting and receiving acoustic energy. The ultrasound data vectors illustrated in FIG. 3 are indicative of acoustic energy emitted and received by the ultrasound transducer in different rotational positions. More specifically, each data vector is representative of ultrasound data collected by the ultrasound transducer at different rotational positions of the ultrasound transducer. As shown in FIG. 3, the ultrasound transducer of catheter 300 may generate ultrasound data on a vector-by-vector basis as the transducer is rotated. For example, the ultrasound transducer may initially acquire an ultrasound data vector 310A and continue to acquire vectors 310B through 310n as the ultrasound transducer is rotated clockwise. Accordingly, vectors 310A-310n are representative of a full 360 degree rotation of the ultrasound transducer. The number of data vectors acquired per rotation may vary depending on the application of the catheter. For example, commercially available IVUS catheters are sometimes configured to generate 512 vectors per rotation wherein the angle between data vectors may then be characterized as approximately $2\pi/512$ radians, or rather $360/512$ degrees. As will be discussed further below, in some examples, a catheter may be configured to generate 4096 vectors per rotation wherein the angle between data vectors may be approximately $2\pi/4096$, or rather $360/4096$ degrees. FIG. 3 also provides a representation of a data frame 303 which is comprised of vectors 310A-310n. A field of view 305 of the catheter 300 may be based on the magnitude of the data vectors propagated by the catheter and may vary to suit a specific application. The magnitude of the data vectors may be based on a number of factors, for example, the frequency of the emitted pressure wave and/or the power level of the pressure wave.

Figure 4:
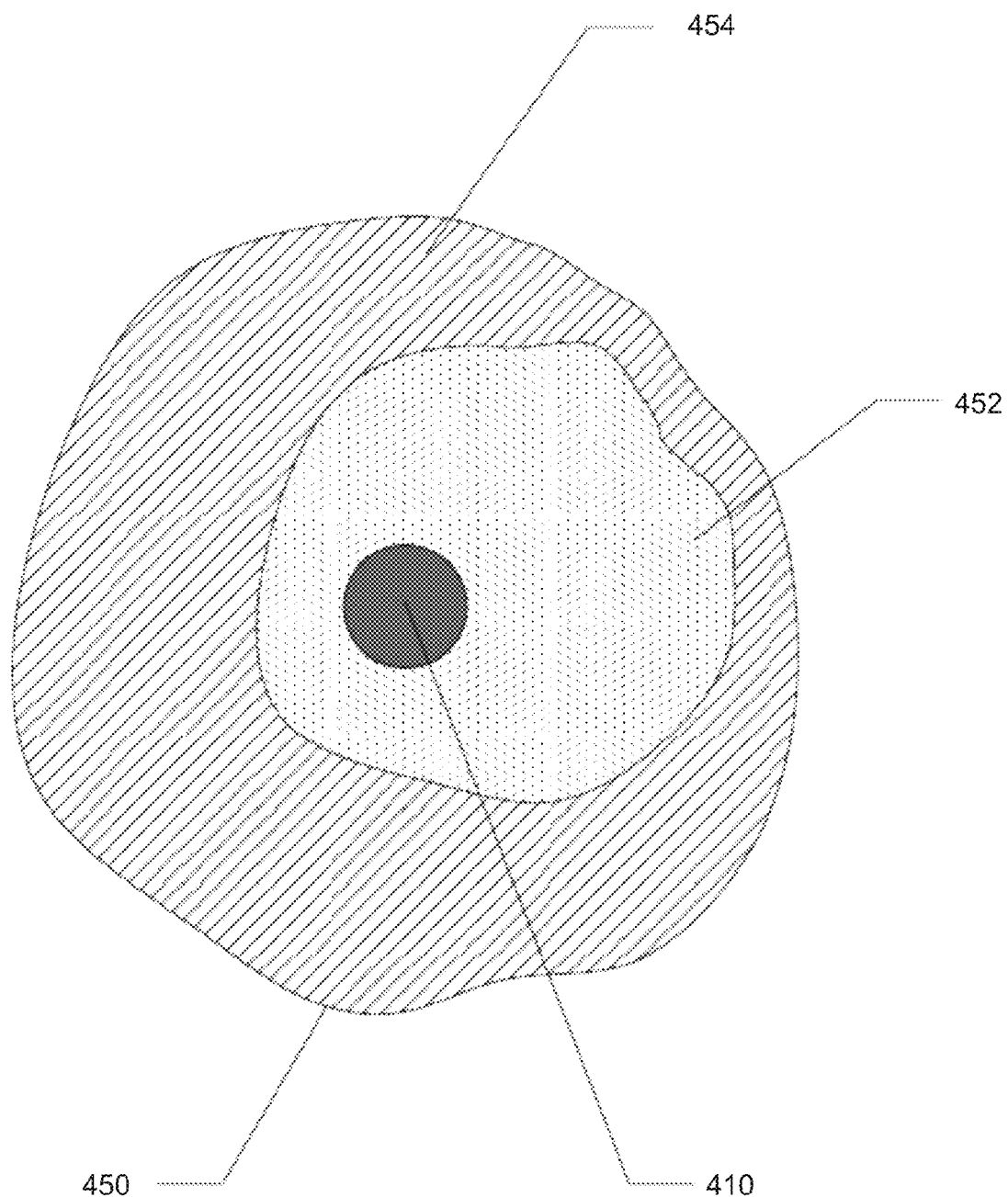
FIG. 4 is a cross-sectional view of a vessel with a catheter in the vessel lumen.

FIG. 4 shows a cross-sectional view of a vessel 450 and a catheter 410 within the vessel. Vessel 450 may be a vessel of a vascular system of a patient including a vessel wall 454 defining a vessel lumen 452, wherein blood flows through the vessel. FIG. 4 also shows catheter 410 positioned in vessel 450. As noted above, catheter 410 may be directly guided into the vessel or, in certain examples, be guided into the vessel via a guide wire.

Figure 5:
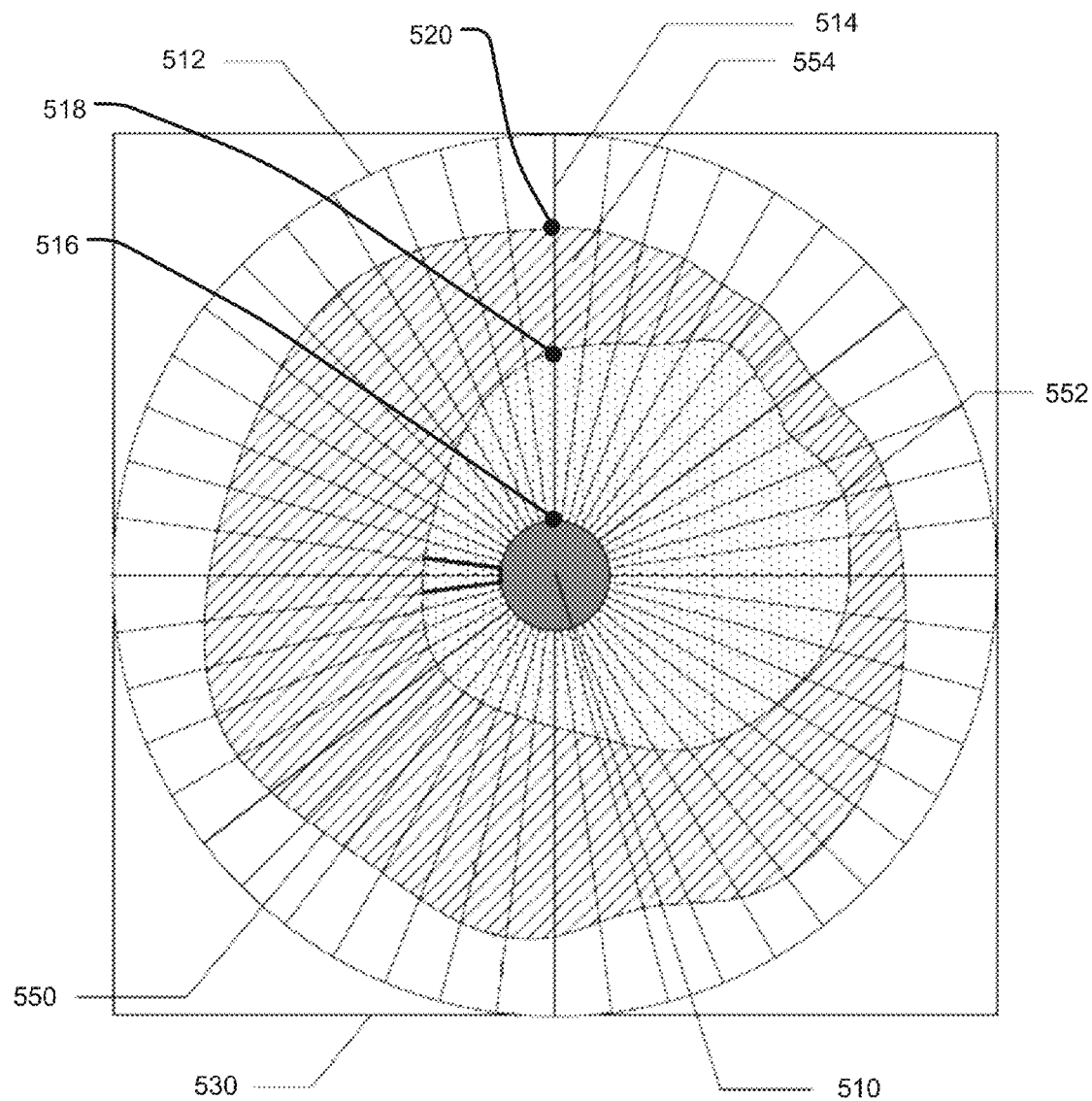
FIG. 5 is a cross-sectional view of vessel with a catheter in the vessel lumen including data vectors propagated by the catheter.

FIG. 5 shows a cross-sectional view of a vessel 550, a catheter 510 within the vessel and an overlay of ultrasound data vectors propagated by the catheter. Vessel 550 is similar to vessel 450 of FIG. 4 and catheter 510 is similar to catheter 300 of FIG. 3. Similar to the examples above, catheter 510 may include an ultrasound transducer configured to generate ultrasound data in the form of a plurality of data vectors. In this example, each data vector corresponds to ultrasound data collected by emitting acoustic energy and receiving of a reflection of the energy, or backscatter, from vessel 550. Different portions of the vessel, for example vessel wall 554 and a fluid in vessel lumen 552, may have different compositions and reflect different amounts of acoustic energy. Variations in ultrasound backscatter levels along a data vector may be used to determine the boundary between the lumen and the wall of a vessel. For example, vessel wall 554 and the fluid within vessel lumen 552 (e.g., blood or contrast) may reflect varying amounts of acoustic energy emitted by the ultrasound transducer of catheter 510. Accordingly, the ultrasound data collected along a data vector may capture the variation in the ultrasound backscatter level between vessel wall 554 and vessel lumen 552. For example, a first region of data vector 514 between data points 516 and 518 may have a backscatter level consistent with blood flowing within the vessel lumen while a second region of data vector 514 between data points 518 and 520 may have a backscatter level consistent with vessel wall 554. Further, the transition between the backscatter levels of the first region and the second region may be used to identify the boundary between vessel wall 554 and vessel lumen 552, located approximately at data point 518. As noted above, data frame 530 may comprise data vectors acquired during a full 360 degree rotation of the ultrasound transducer of catheter 510. Data frame 530 may then be processed by an imaging engine to generate a cross-sectional image of vessel 550.

As noted above, ultrasound data generated by an ultrasound transducer may be affected by a variety of factors including, for example, electrical noise, thermal noise, speckle, and/or relative motion between the vessel and the catheter. These factors may affect the quality of an image generated based on the affected ultrasound data. For example, the boundary between a vessel wall and vessel lumen may appear blurry in such an image. An imaging engine may be configured to perform image enhancement techniques to improve image quality. In particular, frame-based processing and vector domain processing are common image enhancement techniques. Generally, the objective of frame-based processing and vector domain processing techniques is to reduce noise artifacts while minimizing degradation of important image features (e.g., tissue boundaries). Such techniques may use techniques including averaging ultrasound data or envelope averaging to combine ultrasound data to reduce or eliminate image artifacts caused by noise or motion in a vessel.

Figure 6:
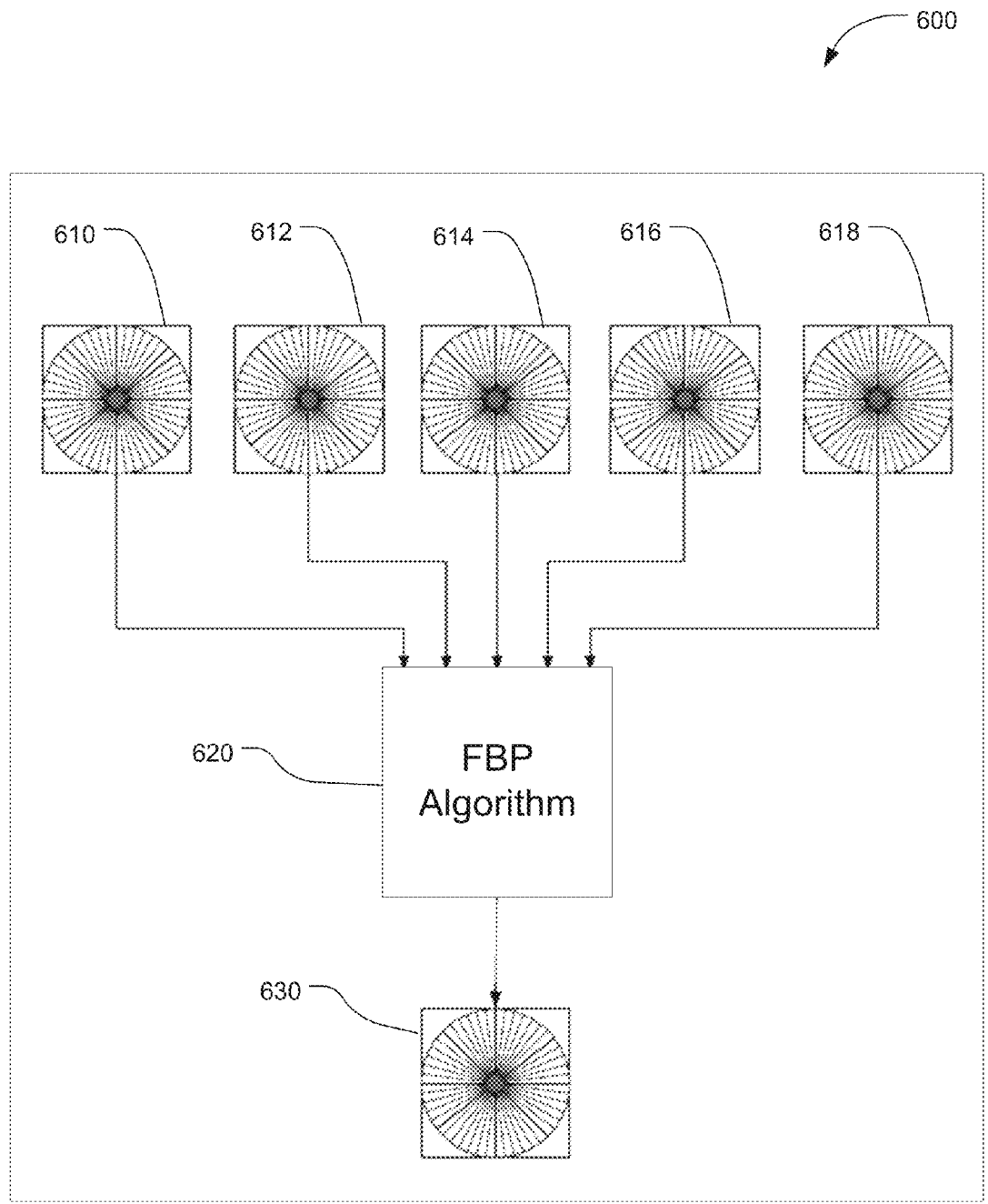
FIG. 6 is a block diagram illustrating an example of frame-based image processing.

FIG. 6 shows a schematic block diagram of an imaging engine 600 performing frame-based image processing (FBP). Generally, FBP approaches to image enhancement combine neighboring image frames to enhance images.

Imaging engine 600 is configured to combine the ultrasound data of data frames 610-618 using a FBP algorithm 620 to produce an enhanced data frame 630. The ultrasound data of enhanced data frame 630 may then be used to generate an image. Generally, an image generated from the ultrasound data of enhanced data frame 630 may contain less image artifacts due to noise. FBP algorithm 620 may employ summing, or averaging, techniques and/or data dependent filters to combine the frames. As shown in FIG. 6, each data frame comprises a plurality of data vectors associated with a complete rotation of the catheter transducer. In one example, imaging engine 600 may generate enhanced data frame 630 by averaging corresponding data vectors from each of data frames 610-618 to generate a corresponding enhanced data vectors of the enhanced frame. Accordingly, enhanced data frame 630 comprises the generated enhanced data vectors.

A disadvantage of FBP is that tissue motion may be non-negligible during the time it takes to acquire multiple data frames. As noted above, FBP may average corresponding data vectors of multiple frames to generate an enhanced data vector. As can be appreciated, averaging more data frames may be more effective at reducing noise in an image than averaging less data frames. Acquiring more data frames, however, requires a period of time that may be long enough such that tissue movement may affect the quality of the image, since each frame generally corresponds with one full rotation of an ultrasound transducer. For example, a real-time IVUS imaging system that provides approximately 25 images per second may have a frame interval of approximately 40 milliseconds (ms). Thus, acquiring five data frames, as in the example of FIG. 6, may take 160 ms. While tissue movement may vary depending on the application, it is probable that tissue movement over this time period will affect the quality of the image. Sacrificing noise reduction by combining less data frames may still not address the issue of tissue movement as vessel wall motion may be on the order of millimeters even between frame acquisitions.

Vector domain techniques are another approach to image enhancement. Unlike FBP, which combines neighboring frames to enhance images, vector domain techniques generally combine neighboring data vectors to generate an enhanced data vector. Because the time between data vectors is orders of magnitude less than the time between data frames, tissue movement between the acquisitions of data vectors is negligible. For example, a catheter configured to acquire 512 data vectors will have an elapsed time of approximately 78 microseconds (µs) between data vectors.

According to some examples, a catheter may be configured to oversample data vectors and combine them using an imaging engine to generate enhanced data vectors. In such examples, oversampled data vectors may be combined by an imaging engine to generate enhanced data vectors that may form an enhanced data frame. For example, a system may include an imaging engine configured to generate an image based on a frame comprising 512 data vectors and a catheter configured to oversample data vectors, acquiring 4096 data vectors per frame. In this example, the catheter is configured to oversample data vectors by a factor of eight. Thus, the imaging engine may be further configured to combine the 4096 oversampled data vectors to generate 512 enhanced data vectors that may then be used to generate an image. According to some examples, the imaging engine may be configured to combine the oversampled data vectors by averaging, or summing. As noted above, the enhanced data vectors may form an enhanced data frame that may then be processed by the imaging engine to generate an enhanced image.

Figure 7:
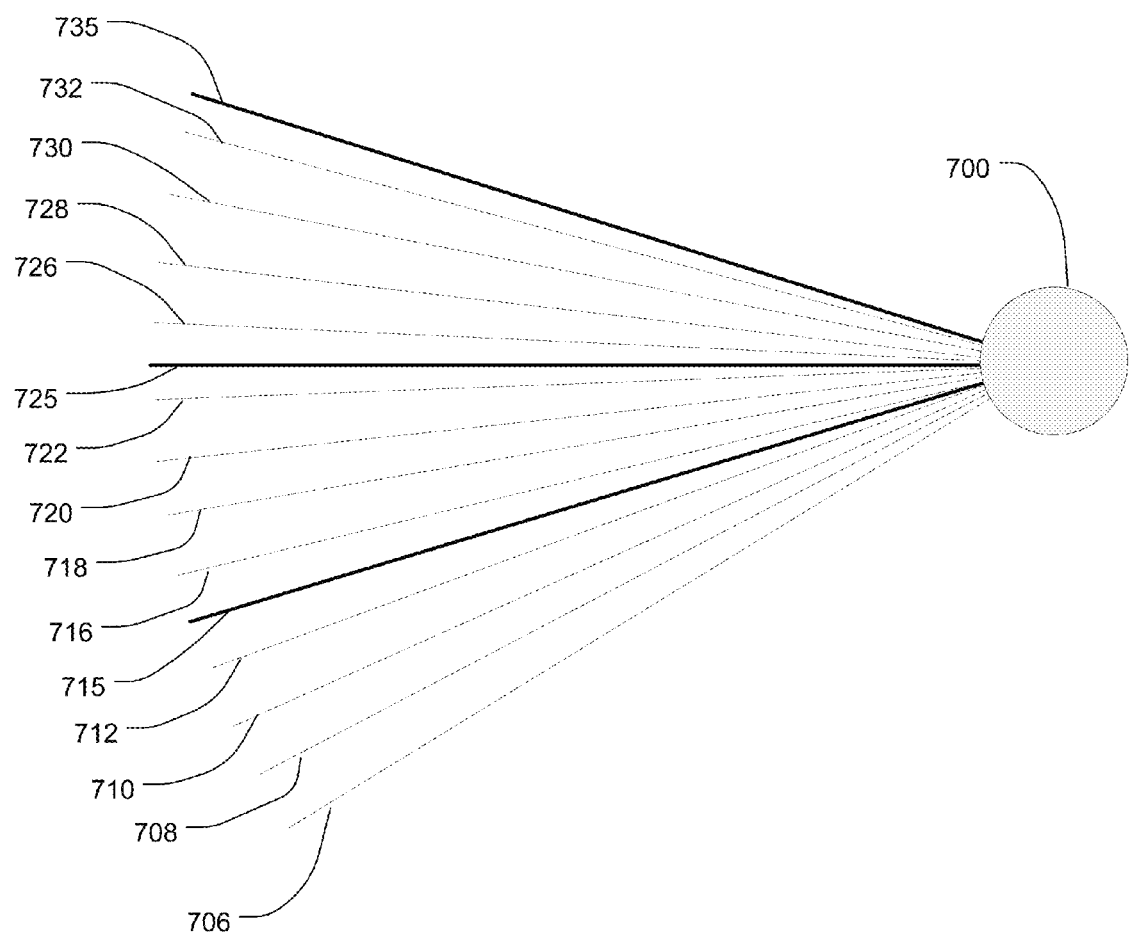
FIG. 7 plan view of a catheter including data vectors propagated by the catheter.

FIG. 7 is shows a catheter 700 according to certain embodiments of the invention that may be suitable for use with vector domain image enhancement techniques. Catheter 700 may be configured to oversample data vectors that may then be combined by an imaging engine to generate enhanced data vectors. In this example, oversampled data vectors 716-722 and 726-732 are represented by dashed lines and enhanced data vectors 715, 725 and 735 are represented by solid lines.

One skilled in the art will appreciate that an imaging engine may be configured to generate an image based on a frame comprising any number of data vectors, enhanced or otherwise. Further, it can be appreciated that a catheter may be configured to oversample data vectors by a variety of factors to suit the needs of different applications. For example, odd oversampling factors (e.g., 3, 5, 7, etc.) may permit the position of enhanced data vectors to be aligned with initial data vectors. Even oversampling factors (e.g., 2, 4, 8, etc.) may be advantageous for hardware and/or software implementations. In one example, with reference to FIG. 7, an imaging engine may combine the four oversampled data vectors 720, 722, 726 and 728 to generate enhanced data vector 725. In another example, an imaging engine may combine eight oversampled data vectors 716-722 and 726-732 to generate enhanced data vector 725. In a different example, an imaging engine may use an oversampled data vector to generate more than one enhanced data vector. For example, oversampled data vectors 708-712 and 716-720 may be used to generate enhanced data vector 715 and oversampled data vectors 718-722 and 726-730 may be used to generate enhanced data vector 725. Thus, oversampled data vectors 718 and 720 are used towards the generation of both enhanced data vectors 725 and 735.

Figure 8:
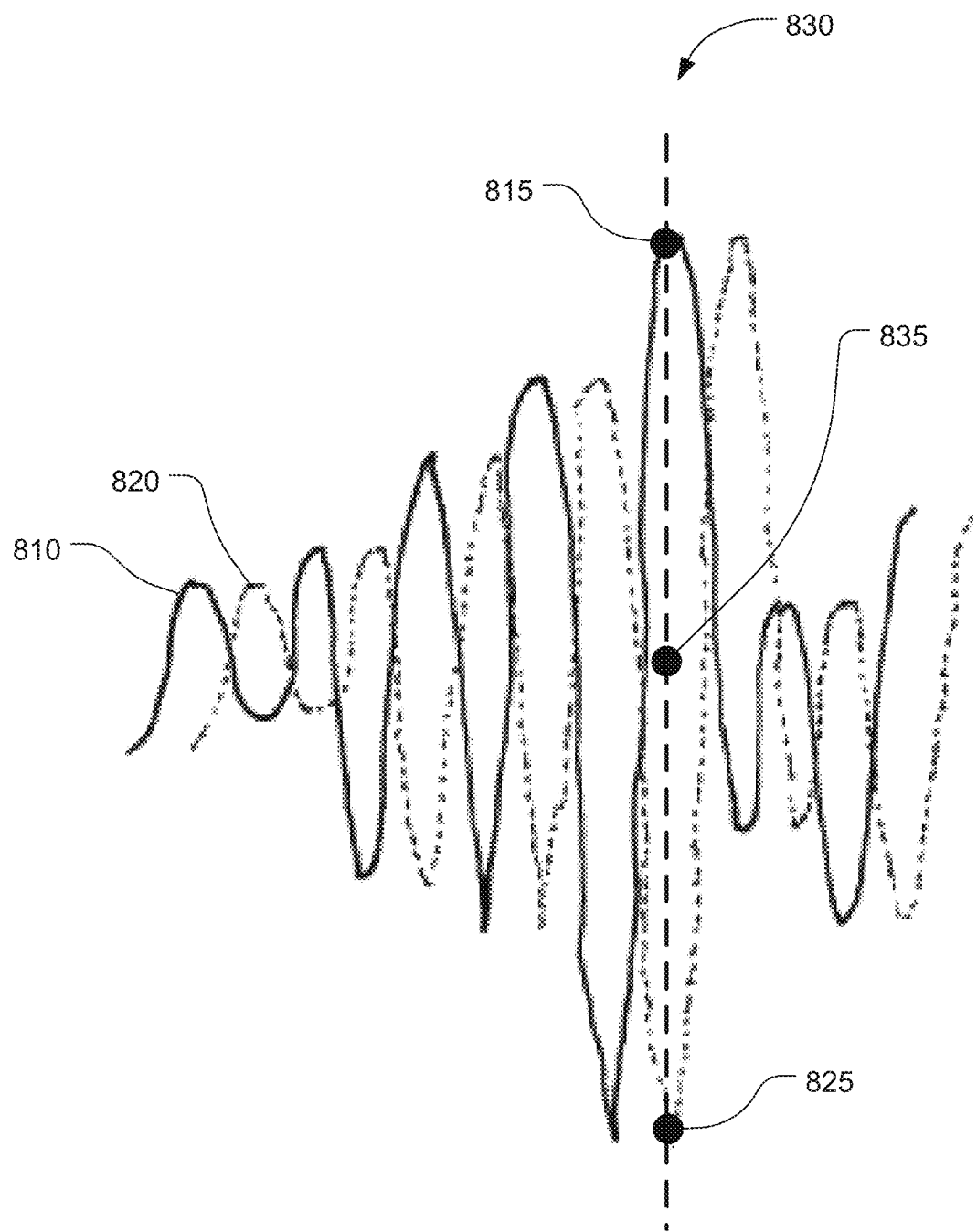
FIG. 8 is a diagram illustrating an example of phase-shifted ultrasound data.

While vector domain image processing generally enhances image quality by reducing noise, it is believed that images generated using vector domain approaches may introduce image artifacts caused by phase cancellation. FIG. 8 illustrates ultrasound data of phase-shifted data vectors that may result in phase cancellation. Ultrasound data 810 is representative of a first data vector and ultrasound data 820 is representative of a second data vector. The first data vector and the second data vector are phase-shifted in such a way that the peaks of ultrasound data 810 may align with the valleys of ultrasound data 820. For example, at point 830, data point 815 of ultrasound data 810 is aligned with data point 825 of ultrasound data 820. Averaging data points 815 and 825 may yield data point 835. As can be appreciated, averaging the data vectors associated with ultrasound data 810 and 820, respectively, may result in phase cancellation in the ultrasound data of an enhanced data vector. In some situations, phase cancellation of ultrasound data may be observable in an enhanced image as darkened spots on the screen.

Figure 9:
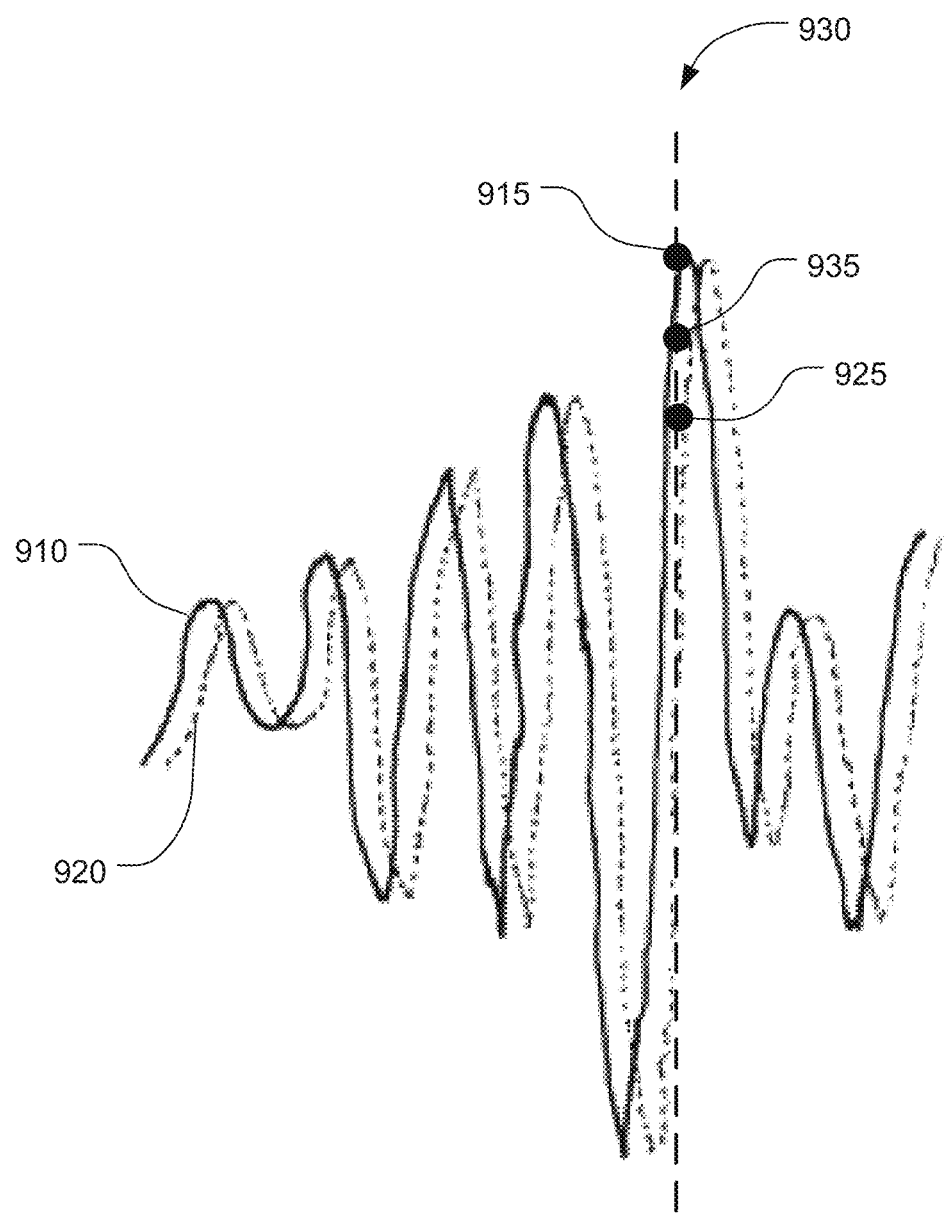
FIG. 9 is a diagram illustrating an example of phase-shifted ultrasound data.

FIG. 9 illustrates ultrasound data of phase-shifted data vectors that do not result in phase cancellation. Ultrasound data 910 is representative of a first data vector and ultrasound data 920 is representative of a second data vector. Unlike the ultrasound data of FIG. 8, ultrasound data 910 and 920 of FIG. 9 may have minimal phase cancellation when averaged. For example, at point 930, data point 915 of ultrasound data 910 is aligned with data point 925 of ultrasound data 920. Averaging data points 915 and 925 may yield data point 935. Accordingly, the degree of phase shifting may be a factor as to whether phase cancellation occurs when data vectors are averaged.

With regard to vector domain techniques for image enhancement, the amount of phase cancellation may be directly proportional to the number of data vectors averaged. More specifically, vector domain techniques wherein neighboring data vectors are averaged may be more susceptible to phase cancellation as the number of data vectors averaged increases. It is believed that image artifacts caused by phase cancellation are more readily observable when more data vectors are averaged or when data vectors taken over a larger angle of the transducer rotation are averaged. For example, with reference to FIG. 7, phase cancellation may be more likely to occur when averaging the eight oversampled data vectors 716-732 than averaging two oversampled data vectors 722 and 726. Thus, while averaging more data vectors may be more effective at reducing noise, it may also introduce image artifacts due to phase cancellation. Averaging less data vectors may be less likely to introduce image artifacts caused by phase cancellation, but has the disadvantage of being less effective at reducing noise in an image.

Figure 10:
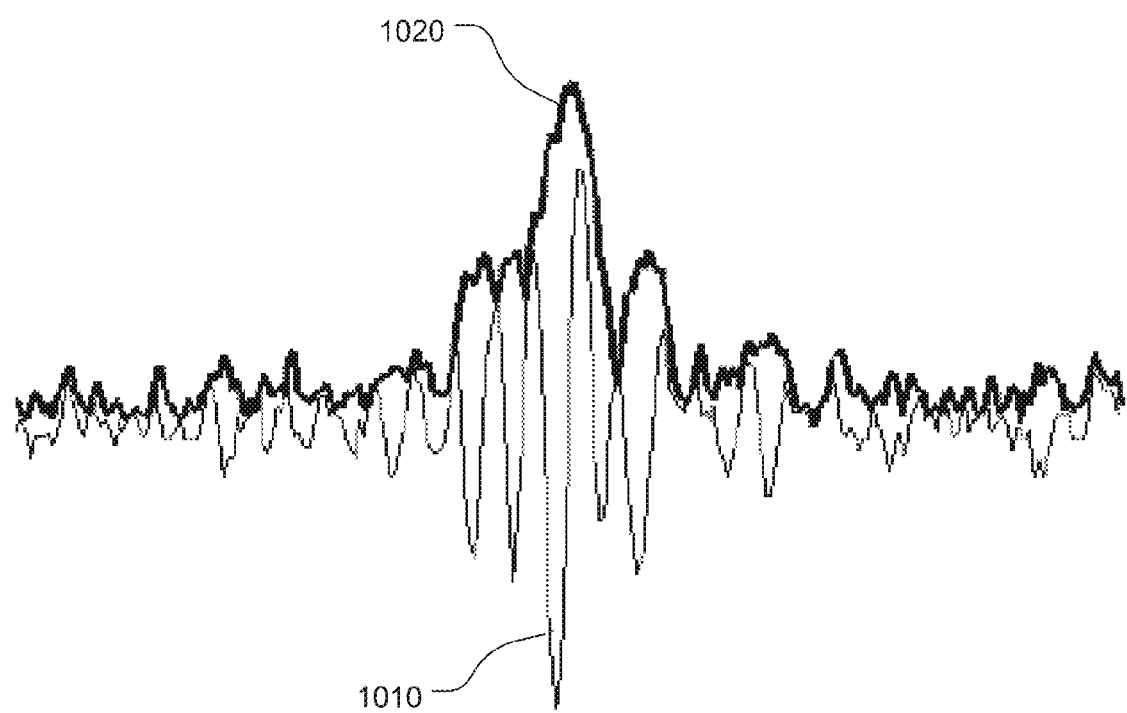
FIG. 10 is a diagram illustrating ultrasound data and a corresponding envelope of the ultrasound data.

In certain embodiments of the present invention, phase cancellation between data vectors may be reduced by generating an envelope of each data vector and then averaging the envelopes. Because envelopes are expressed in magnitude, and not amplitude, phase cancellation is not an issue where detected envelopes associated with data vectors are averaged. FIG. 10 shows an example of ultrasound data 1010 and a corresponding envelope 1020. Ultrasound data 1010 may be representative of a data vector and an imaging engine may be configured to detect an envelope of ultrasound data 1010 to generate envelope 1020. According to some examples, an envelope may be detected by demodulating the ultrasound data of the data vector. In some examples, demodulation may include bandpass filtering, down-mixing, low-pass filtering and decimation. It can be appreciated, however, that any suitable method for envelope detection, or for demodulation, known in the art may be used depending on the application. One potential consequence with this method is that detecting an envelope of each data vector may be resource intensive due to the operations necessary to detect an envelope.

Figure 11:
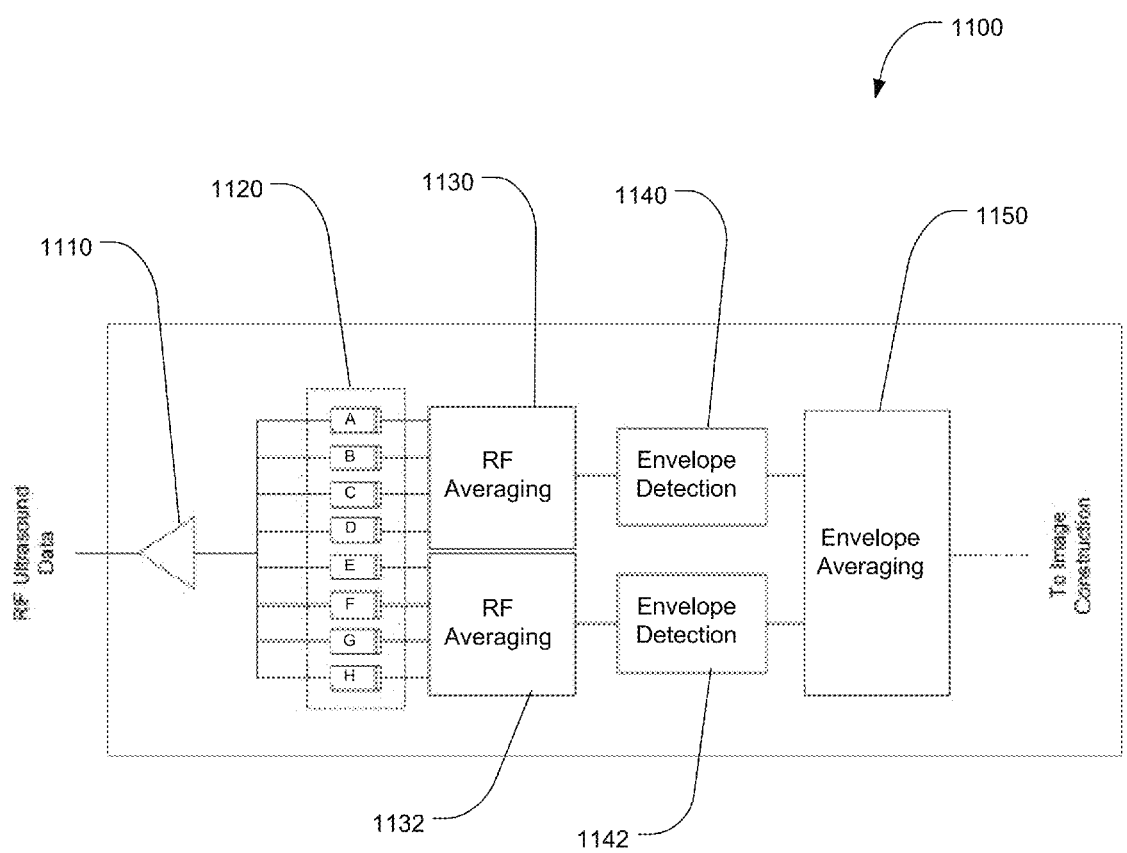
FIG. 11 is a block diagram illustrating a method for processing an image based on ultrasound data.

According to some embodiments of the present invention, an image enhancing technique may utilize averaging of ultrasound data and of envelope averaging. FIG. 11 shows an imaging engine 1100 configured to generate an image based on ultrasound data. More specifically, imaging engine 1100 may be configured to generate an enhanced image by combining ultrasound data associated with eight data vectors by averaging. Imaging engine 1100 may comprise at least one processor (not shown), an analog to digital (A/D) conversion unit 1110 and memory module 1120. In this example, a catheter including an ultrasound transducer may acquire data vectors and communicate the ultrasound data associated with the data vectors to imaging engine 1100. Imaging engine 1100 may receive and convert the ultrasound data into digital data using A/D conversion unit 1110. As ultrasound data is acquired and converted, the digital data may be stored in memory module 1120. For example, the ultrasound transducer may acquire ultrasound data associated with a first data vector and communicate the data to imaging engine 1100. The imaging engine may then convert the ultrasound data of the first data vector to digital data and store the digital data into memory unit 1120A. Similarly, the ultrasound transducer may acquire a second data vector, communicate the ultrasound data associated with the second data vector to imaging engine 1100 which may then convert the data into digital data and store the digital data into memory unit 1120B. These steps may be repeated until eight data vectors have been received, converted and stored in memory units 1120A-H. It can be appreciated that memory units 1120A-H need not be physically separate memory modules and that they are used only for illustrative purposes to demonstrate a method for storing the digital data in such a way that the digital data associated with respective data vectors may be individually accessed. In some examples, each of the memory units may be included in a single memory module 1120. In other examples, each memory units 1120A-H may be a physically separate memory module, or the memory units may be distributed across a plurality of memory modules.

Imaging engine 1100 may then combine the ultrasound data of the data vectors in steps 1130 and 1132 using at least one programmable processor. In this example, step 1130 may comprise averaging the digital data representative of the first four data vectors stored in memory units 1120A-D, and step 1130 may comprise averaging the digital data representative of the last four data vectors stored in memory units 1120E-H. As noted above, the amount of phase cancellation may be directly proportional to the number of data vectors averaged. As applied to this example, phase cancellation may be more likely to occur if the ultrasound data of memory units 1120A-H are averaged in comparison to averaging the ultrasound data of memory units 1120A-D. Thus, separately grouping and averaging the ultrasound data of the first four and last four data vectors stored in memory units 1120A-D and E-H, respectively, may minimize or eliminate phase cancellations due to averaging of ultrasound data.

Imaging engine 1100 may then generate an envelope in steps 1140 and 1142 of the averaged ultrasound data generated from steps 1130 and 1132, respectively. As noted above, detecting an envelope may comprise demodulating the ultrasound data and may include, according to some examples, the steps of bandpass filtering, down-mixing, low-pass filtering and decimation. The imaging engine may then generate an enhanced data vector by averaging the detected envelopes in step 1150 thus generating an enhanced data vector. As can be appreciated, imaging engine 1100 may generate additional enhanced data vectors by repeating the steps shown in FIG. 11 and generate an image based on the enhanced data vectors. For example, a system including an ultrasound transducer configured to acquire 4026 oversampled data vectors and an imaging engine configured to generate an image based on a frame comprising 512 data vectors may repeat the steps shown in FIG. 11 512 times to generate the appropriate number of enhanced data vectors to generate an enhanced data frame.

One skilled in the art will appreciate that FIG. 11 only shows one example of an imaging engine configured to combine data vectors to generate an enhanced data vector and does not limit the scope of this application. For example, the steps in FIG. 11 may be modified to receive any number of data vectors and generate an enhanced data vector based on the received data vectors as appropriate for a specific application. Accordingly, an imaging engine may include one or more memory modules to accommodate an appropriate number of memory units to store the ultrasound data associated with the received data vectors. Further, the order in which ultrasound data is received and stored in the memory units as provided in FIG. 11 and described above is intended for illustrative purposes only and does not limit the manner in which the ultrasound data may be stored within the memory unit.

It should be appreciated that the digital data associated with the received data vectors may be averaged in any combination and the number and is not limited to the sets illustrated in FIG. 11 (i.e., 1120A-D, 1120E-H). For example, the ultrasound data associated with the received data need not be divided into two sets as shown in FIG. 11, but may be divided into any number of sets of data vectors as suitable for a specific application. Further, each set need not be associated with the same number of data vectors. For example, with reference to FIG. 11, the memory units may be divided into three sets comprising 1120A-C, 1120D-F, and 1120G-H, wherein two sets include three memory units and one set includes two memory units. Also, the sets need not comprise radially sequential ultrasound data vectors. For example, where memory units 1120A-H comprise digital data associated with radially sequential data vectors from A to H, a first set may comprise memory units 1120A, 1120C, 1120E and 1120G and a second set may comprise memory units 1120B, 1120D, 1120F, and 1120H. In some examples, the grouping of ultrasound data vectors into sets may take into account which data vectors are least likely to cause phase cancellation when averaged. Further, the sets need not be exclusive in that an imaging may be configured to use ultrasound data associated with a received data vector in more than one set. For example, with reference to FIG. 11, a first set may comprise memory units 1120A-E, and a second set may comprise memory units 1120D-H, such that memory units 1120D and 1120E are present in two sets. In another example, the digital data stored in each memory unit 1120A-H need not be unique or generated from distinct data vectors. For example, imaging engine 1100 may be configured to receive a data vector and convert the data vector into digital data, then store the digital data of the data vector into both memory units 1120D and 1120E.

In one example, the number of sets formed from the received ultrasound data associated with the data vectors may vary. For example, an imaging engine may be configured to generate an enhanced data vector using a method similar to the method of FIG. 11 using the ultrasound data associated with eight data vectors. In this example, the imaging engine may generate a first enhanced data vector based on the first eight data vectors received from the ultrasound transducer by dividing the eight data vectors into two sets. Accordingly, two envelopes may be generated based on the two sets and then averaged to form a first enhanced data vector. However, in generating a second enhanced vector based on the next eight data vectors received from the ultrasound transducer, the imaging engine may divide the received ultrasound data associated with the eight data vectors into four sets. Thus, the second enhanced data vector may be generated by averaging four envelopes generated from the four sets. In certain examples, an imaging engine may dynamically select the number of sets to form, the number of data vectors associated with each set, as well as which data vectors to include in each set. This dynamic selection may be based on grouping together data vectors that are least likely to cause phase cancellation and may be based on predetermined knowledge or in, for example, a dynamic evaluation of the ultrasound data.

One skilled in the art will appreciate that the techniques described in this disclosure may be implemented, at least in part, in hardware, software, firmware or any combination thereof. For example, various aspects of the described techniques may be implemented within one or more processors, including one or more microprocessors, digital signal processors (DSPs), application specific integrated circuits (ASICs), field programmable gate arrays (FPGAs), or any other equivalent integrated or discrete logic circuitry, as well as any combinations of such components. The term "processor" may generally refer to any of the foregoing logic circuitry, alone or in combination with other logic circuitry, or any other equivalent circuitry. A control unit comprising hardware may also perform one or more of the techniques of this disclosure.

Such hardware, software, and firmware may be implemented within the same device or within separate devices to support the various operations and functions described in this disclosure. In addition, any of the described units, modules or components may be implemented together or separately as discrete but interoperable logic devices. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components.

Further, the techniques described in this disclosure may also be embodied or encoded in a non-transitory computer-readable medium, such as a computer-readable storage medium, containing instructions. Instructions embedded or encoded in a computer-readable storage medium may cause a programmable processor, or other processor, to perform the method, e.g., when the instructions are executed. Non-transitory computer readable storage media may include volatile and/or non-volatile memory forms including, e.g., random access memory (RAM), read only memory (ROM), programmable read only memory (PROM), erasable programmable read only memory (EPROM), electronically erasable programmable read only memory (EEPROM), flash memory, a hard disk, a CD-ROM, a floppy disk, a cassette, magnetic media, optical media, or other computer readable media.

Various examples of the invention have been described. Although the present invention has been described in considerable detail with reference to certain disclosed embodiments, the embodiments are presented for purposes of illustration and not limitation. Other embodiments incorporating the invention are possible. One skilled in the art will appreciate that various changes, adaptations, and modifications may be made without departing from the spirit of the invention and the scope of the appended claims.

The invention claimed is:

1. An imaging system comprising:
an ultrasound transducer configured to rotate and acquire a plurality of data vectors in a single rotation of the ultrasound transducer by emitting acoustic energy and receiving a backscatter of the acoustic energy, each data vector comprising ultrasound data, the plurality of data vectors acquired in the single rotation making up a single frame;
an imaging engine comprising at least one processor, the imaging engine configured to:
receive the plurality of data vectors of the single frame from the ultrasound transducer;
form a first set of data vectors of the single frame and a second set of data vectors of the single frame from the plurality of data vectors, wherein a first data vector of the first set of data vectors differs from a second data vector of the second set of data vectors in that the first data vector is acquired at a first radial location that is different from a second radial location at which the second data vector is acquired during the single rotation of the ultrasound transducer;

generate, using the at least one processor, a first combination of data based on the first set of data vectors and a second combination of data based on the second set of data vectors;

generate, using the at least one processor, a first envelope based on the first combination of data and a second envelope based on the second combination of data;

generate, using the at least one processor, a combined envelope based on the first envelope and the second envelope, wherein the combined envelope is generated using only data of the single frame, and wherein the combined envelope represents data from the different radial locations; and generate, using the at least one processor, an image based on the combined envelope.

2. The imaging system of claim 1, further comprising:
a catheter assembly configured to deliver the ultrasound transducer to an imaging area; and
a patient interface module including a catheter interface, wherein the patient interface module is electrically connected to the imaging engine and is coupled to the catheter assembly and the ultrasound transducer via the catheter interface; and
wherein the patient interface module is configured to rotate the ultrasound transducer relative to the catheter assembly.

3. The imaging system of claim 1, wherein the data vectors of the first set of data vectors are circumferentially adjacent and the data vectors of the second set of data vectors are circumferentially adjacent.

4. The imaging system of claim 2, wherein the ultrasound transducer is configured to acquire data vectors every $2\pi/4096$ radians as it is rotated relative to the catheter assembly.

5. The imaging system of claim 1, wherein the first set of data vectors includes two data vectors and the second set of data vectors includes two data vectors.

6. The imaging system of claim 1, wherein the first set of data vectors includes four data vectors and the second set of data vectors includes four data vectors.

7. The imaging system of claim 1, wherein the first set of data vectors and the second set of data vectors each include at least one common data vector.

8. The imaging system of claim 1, wherein the first combination of data is generated by averaging the ultrasound data associated with each data vector of the first set of data vectors and the second combination of data is generated by averaging the ultrasound data associated with each data vector of the second set of data vectors.

9. The imaging system of claim 1, wherein the combined envelope is generated by averaging the first envelope and the second envelope.

10. The imaging system of claim 1, wherein the acoustic energy emitted by the ultrasound transducer is between 40-60 MHz.

11. A method comprising:
rotating a ultrasound transducer to acquire a plurality of data vectors in a single rotation of the ultrasound transducer, the plurality of data vectors acquired in the single rotation making up a single frame;
forming a first set of data vectors of the single frame and a second set of data vectors of the single frame from the plurality of data vectors, wherein a first data vector of the first set of data vectors differs from a second data vector of the second set of data vectors in that the first data vector is acquired at a first radial location that is different from a second radial location at which the second data vector is acquired during the single rotation of the ultrasound transducer;

generating a first combination of data based on the first set of data vectors and a second combination of data based on the second set of data vectors;

generating a first envelope based on the first combination of data and a second envelop based on the second combination of data;

generating a combined envelope based on the first envelope and the second envelope, wherein the combined envelope is generated using only data of the single frame, and wherein the combined envelope represents data from the different radial locations; and generating an image based on the combined envelope.

12. The method of claim 11, wherein the data vectors of the first set of data vectors are circumferentially adjacent and the data vectors of the second set of data vectors are circumferentially adjacent.

13. The method of claim 12, wherein circumferentially adjacent data vectors are separated by $2\pi/4096$ radians.

14. The method of claim 11, wherein the first set of data vectors includes two data vectors and the second set of data vectors includes two data vectors.

15. The method of claim 11, wherein the first set of data vectors includes four data vectors and the second set of data vectors includes four data vectors.

16. The method of claim 11, wherein the first set of data vectors and the second set of data vectors each include at least one common data vector.

17. The method of claim 11, wherein the step of generating the first combination of data comprises averaging the ultrasound data associated with the data vectors of the first set of data vectors and the step of generating the second combination of data comprises averaging the ultrasound data associated with the data vectors of the second set of data vectors.

18. The method of claim 11, wherein the step of generating the combined envelope further comprises averaging the first envelope and the second envelope.

19. The method of claim 11, wherein the step of generating the first envelope comprises demodulating the first combination of data and the step of generating the second envelope comprises demodulating the second combination of data.

20. A non-transitory computer-readable storage article having computer-executable instructions stored thereon to cause at least one programmable processor to:
receive a plurality of data vectors acquired during a single rotation of an ultrasound transducer, wherein each data vector comprises ultrasound data, the plurality of data vectors acquired in the single rotation making up a single frame;
form a first set of data vectors of the single frame and a second set of data vectors of the single frame from the plurality of data vectors, wherein a first data vector of the first set of data vectors differs from a second data vector of the second set of data vectors in that the first data vector is acquired at a first radial location that is different from a second radial location at which the second data vector is acquired during the single rotation of the ultrasound transducer;

generate a first combination of data based on the first set of data vectors and a second combination of data based on the second set of data vectors;

generate a first envelope based on the first combination of data and a second envelope based on the second combination of data;

generate a combined envelope based on the first envelope and the second envelope, wherein the combined envelope is generated using only data of the single frame, and wherein the combined envelope represents data from the different radial locations; and generate an image based on the combined envelope.

21. The article of claim 20, wherein the data vectors of the first set of data vectors are circumferentially adjacent and the data vectors of the second set of data vectors are circumferentially adjacent.

22. The article of claim 21, wherein circumferentially adjacent data vectors are separated by $2\pi/4096$ radians.

23. The article of claim 20, wherein the first set of data vectors includes two data vectors and the second set of data vectors includes two data vectors.

24. The article of claim 20, wherein the first set of data vectors includes four data vectors and the second set of data vectors includes four data vectors.

25. The article of claim 20, wherein the first set of data vectors and the second set of data vectors each include at least one common data vector.

26. The article of claim 20, further comprising executable instructions to cause the at least one processor to generate the first combination of data by averaging the ultrasound data associated with the data vectors of the first set of data vectors and generate the second combination of data by averaging the ultrasound data associated with the data vectors of the second set of data vectors.

27. The article of claim 20, further comprising executable instructions to cause the at least one processor to generate the first envelope by demodulating the first combination of data and generate the second envelope by demodulating the second combination data.

28. The article of claim 20, further comprising executable instructions to cause the at least one processor to generate the combined envelope by averaging the first envelope and the second envelope.

* * * * *

UNITED STATES PATENT AND TRADEMARK OFFICE
CERTIFICATE OF CORRECTION

| | | |
|---|---|---|
| PATENT NO. | : 9,693,754 B2 | Page 1 of 1 |
| APPLICATION NO. | : 13/894927 | |
| DATED | : July 4, 2017 | |
| INVENTOR(S) | : Duc H. Lam et al. | |

It is certified that error appears in the above-identified patent and that said Letters Patent is hereby corrected as shown below:

On the Title Page

Item (72), Inventor, please add --J. Steve Reynolds, Milpitas, CA (US)--

Signed and Sealed this
Seventeenth Day of October, 2017

Joseph Matal
*Performing the Functions and Duties of the*
*Under Secretary of Commerce for Intellectual Property and*
*Director of the United States Patent and Trademark Office*